US011439529B2

(12) United States Patent
Pavini (10) Patent No.: US 11,439,529 B2
(45) Date of Patent: Sep. 13, 2022

(54) MEDICAL PROTECTIVE AND EXERCISE RESTRAINT METHODS (71) Applicant: Marie Pavini, Chittenden, VT (US)

(72) Inventor: Marie Pavini, Chittenden, VT (US)

(*) Notice: Subject to any disclaimer, the term of this patent is extended or adjusted under 35 U.S.C. 154(b) by 220 days.

(21) Appl. No.: 16/860,934

(22) Filed: Apr. 28, 2020

(65) Prior Publication Data
US 2020/0253775 A1 Aug. 13, 2020

Related U.S. Application Data (62) Division of application No. 15/237,325, filed on Aug. 15, 2016, now Pat. No. 10,646,369.
(Continued)

(51) Int. Cl.
A61F 5/37 (2006.01)
A63B 21/04 (2006.01)
(Continued)

(52) U.S. Cl.
CPC .......... A61F 5/373 (2013.01); A63B 21/0004 (2013.01); A63B 21/028 (2013.01); A63B 21/0442 (2013.01); A63B 21/0552 (2013.01); A63B 21/4005 (2015.10); A63B 21/4017 (2015.10); A63B 21/4019 (2015.10);
(Continued)

(58) Field of Classification Search
CPC .............. A61F 5/05841; A61F 5/05858; A61F 5/0585; A61F 5/05866; A61F 5/05875; A61F 5/05; A61F 5/3723; A61F 5/373; A61F 5/37; A63B 23/1245; A63B 23/03508; A63B 23/16; A63B 21/4005; A63B 21/4017; A63B 21/4019; A63B 21/4023; A63B 21/4033; A63B 21/0004;
(Continued)

(56) References Cited

U.S. PATENT DOCUMENTS 1,073,478 A 9/1913 Dodd
1,340,630 A 5/1920 Maddox
(Continued)

FOREIGN PATENT DOCUMENTS

GB 1150072 A 4/1969
WO 2012118423 A1 9/2012
(Continued)

OTHER PUBLICATIONS

International Search Report and Written Opinion dated Oct. 28, 2016, in connection with PCT/US16/47090, filed Aug. 15, 2016.
(Continued)

Primary Examiner — Camtu T Nguyen
(74) Attorney, Agent, or Firm — Downs Rachlin Martin PLLC (57) ABSTRACT Intended to prevent self-extubation of nasal or oral tubes of an awake patient who may reflexively attempt removal of such and allow the early mobilization and exercise necessary for preservation of as much muscle strength as possible, promotion of diaphragmatic motion necessary for liberation from a ventilator, reduction of patient stress allowing for sedation minimization and improved cognition for reduction of delirium and post-intensive care syndrome, and relief of medical staff and healthcare dollars to focus more on healthcare rather than on protection from self-harm.

9 Claims, 10 Drawing Sheets

Related U.S. Application Data (60) Provisional application No. 62/205,298, filed on Aug. 14, 2015.

(51) Int. Cl.

| | | |
|---|---|---|
| *A63B 23/035* | (2006.01) | |
| *A63B 21/055* | (2006.01) | |
| *A63B 23/12* | (2006.01) | |
| *A63B 21/00* | (2006.01) | |
| *A63B 21/02* | (2006.01) | |
| *A63B 23/16* | (2006.01) | |
| *A63B 22/00* | (2006.01) | |
| *A63B 71/00* | (2006.01) | |

(52) U.S. Cl.
CPC ...... *A63B 21/4023* (2015.10); *A63B 21/4033* (2015.10); *A63B 23/03508* (2013.01); *A63B 23/1245* (2013.01); *A63B 23/16* (2013.01); *A63B 2022/0094* (2013.01); *A63B 2071/0072* (2013.01); *A63B 2225/09* (2013.01); *A63B 2230/30* (2013.01)

(58) Field of Classification Search
CPC .............. A63B 21/028; A63B 21/0442; A63B 21/0552
See application file for complete search history.

(56) References Cited

U.S. PATENT DOCUMENTS

| | | | |
|---|---|---|---|
| 1,431,915 A | 10/1922 | DeBarr | |
| 1,643,850 A | 9/1927 | Jones | |
| 1,887,022 A | 11/1932 | Hoffman et al. | |
| 1,921,987 A | 8/1933 | Ettinger | |
| 2,191,283 A | 2/1940 | Longfellow | |
| 2,266,230 A | 12/1941 | Mazzeo et al. | |
| 2,551,617 A | 5/1951 | Maybert | |
| 2,590,739 A | 3/1952 | Wagner et al. | |
| 2,693,794 A | 11/1954 | Neville | |
| 2,744,526 A | 12/1954 | Saylors | |
| 2,703,082 A * | 3/1955 | Emert | A61F 5/373 |
| | | | 473/214 |
| 3,010,452 A | 11/1961 | Smith | |
| 3,196,870 A | 7/1965 | Sprecher et al. | |
| 3,256,880 A | 6/1966 | Caypinar | |
| 3,439,673 A | 4/1969 | Sprecher | |
| 3,480,013 A | 11/1969 | Garber | |
| 3,540,719 A | 11/1970 | Romney | |
| 3,625,210 A | 12/1971 | Mikkelson | |
| 3,812,851 A | 5/1974 | Rodriguez | |
| 4,078,560 A | 3/1978 | Hill | |
| 4,503,849 A | 3/1985 | Morgan et al. | |
| 4,615,339 A | 10/1986 | Siwek | |
| 4,899,735 A | 2/1990 | Townsend et al. | |
| 4,941,460 A | 7/1990 | Working | |
| 5,025,801 A | 6/1991 | Callaway | |
| 5,038,764 A | 8/1991 | Paez | |
| 5,083,575 A | 1/1992 | Jones | |
| 5,337,737 A | 8/1994 | Rubin et al. | |
| 5,358,471 A | 10/1994 | Klotz | |
| 5,383,844 A | 1/1995 | Munoz et al. | |
| 5,456,268 A | 10/1995 | Bonutti | |
| 5,662,594 A | 9/1997 | Rosenblatt | |
| 5,759,165 A | 6/1998 | Malewicz | |
| 5,845,643 A | 12/1998 | Vergano et al. | |
| 5,848,979 A | 12/1998 | Bonutti et al. | |
| 5,944,677 A | 8/1999 | Richard | |
| 5,951,499 A * | 9/1999 | Saringer | A61H 1/0274 |
| | | | 601/5 |
| 6,000,402 A | 12/1999 | Able | |
| 6,244,271 B1 | 6/2001 | Turner | |
| 6,293,918 B1 | 9/2001 | Wang | |
| 6,530,868 B1 | 3/2003 | Pape | |
| 6,533,741 B1 | 3/2003 | Lee et al. | |
| 6,936,020 B2 | 8/2005 | Davis | |
| 7,101,347 B2 | 9/2006 | Culhane et al. | |
| 7,207,960 B2 | 4/2007 | Kenney | |
| 7,416,537 B1 | 8/2008 | Stark et al. | |
| 7,476,102 B2 | 1/2009 | Maples | |
| 7,789,844 B1 | 9/2010 | Allen | |
| 7,850,632 B2 | 12/2010 | Gilmour | |
| 7,931,609 B2 | 4/2011 | Blanchard | |
| 7,942,839 B2 | 5/2011 | Cohen et al. | |
| 8,273,043 B2 | 9/2012 | Bonutti et al. | |
| 8,322,342 B2 | 12/2012 | Soto et al. | |
| 8,622,945 B2 | 1/2014 | Meals | |
| 8,640,707 B2 | 2/2014 | Rozier et al. | |
| 9,114,277 B2 | 8/2015 | Goeckel | |
| 2003/0125651 A1 | 7/2003 | Hopkins et al. | |
| 2004/0149293 A1 | 8/2004 | Freedman | |
| 2005/0080369 A1 | 4/2005 | Kim | |
| 2005/0101895 A1 | 5/2005 | Patel | |
| 2005/0165337 A1 | 7/2005 | Weiss | |
| 2006/0009724 A1 | 1/2006 | Busuttil | |
| 2006/0200061 A1 | 9/2006 | Warkentine | |
| 2006/0258965 A1 | 11/2006 | Lee et al. | |
| 2006/0276735 A1 | 12/2006 | Phelen | |
| 2007/0106189 A1 | 5/2007 | Salmon | |
| 2007/0156070 A1 | 7/2007 | Schwab | |
| 2009/0062707 A1 | 3/2009 | Busuttil | |
| 2014/0060547 A1 | 3/2014 | Vallino et al. | |
| 2014/0083437 A1 | 3/2014 | Hall et al. | |
| 2014/0194798 A1 | 7/2014 | Sotereanos | |
| 2014/0305442 A1 | 10/2014 | Berdenudd et al. | |
| 2015/0088045 A1 | 3/2015 | Laurensse | |

FOREIGN PATENT DOCUMENTS

| | | |
|---|---|---|
| WO | 2012125702 A2 | 9/2012 |
| WO | 2014100155 A1 | 6/2014 |

OTHER PUBLICATIONS

European Search Report and Written Opinion dated Mar. 19, 2019, in connection with EP16837667.

\* cited by examiner

MEDICAL PROTECTIVE AND EXERCISE RESTRAINT METHODS

RELATED APPLICATION DATA

This application is a divisional application of U.S. Non-provisional patent application Ser. No. 15/237,325, filed Aug. 15, 2016, and titled "Medical Protective and Exercise Restraint Systems and Methods", and which application claims the benefit of priority of U.S. Provisional Patent Application Ser. No. 62/205,298, filed on Aug. 14, 2015, and titled "Protective And Exercise Restraint System For Intubated Patients". Each of these applications is incorporated by reference herein in its entirety.

FIELD OF THE INVENTION

The present invention generally relates to the field of medical restraining devices. In particular, the present invention is directed to medical protective and exercise restraint systems and methods for, e.g., intubated patients or patients who otherwise have indwelling tubes, lines, or catheters.

BACKGROUND

For intubated intensive care unit patients confined to a bed for any significant period of time, meaningful early mobilization and sedation minimization are key elements in reducing morbidity and mortality, hastening recovery and improving quality of life by preserving cognition and strength. However, when breathing tubes, naso/orogastric tubes, intravenous (IV) lines and other medical devices are in place, preventing removal (e.g., self-extubation) of such devices can also reduce morbidity and mortality in, e.g., an intensive care unit (ICU). In order to prevent removal, restraints that drastically restrict the patient's range of motion are often used and sedation is then administered to reduce the anxiety of being unable to move. Caregiver personnel are reluctant to loosen or remove restraints because of the dire consequences of premature medical device disconnection, thereby presenting a dilemma in balancing these competing concerns.

Various types of restraints have been employed in an attempt to permit a reasonable range of motion while still protecting against device removal by the patient. However, existing restraint systems that do allow for reasonable motion still do not provide reliable or sufficient protection against device removal, nor do they allow changeable and graded levels of restraint to follow a patient's changing capabilities such that a mandate of minimum patient restraint is continually followed. For example, mitt restraints are often ineffective as patients can still disconnect themselves by pressing the mitts together. In fact even with wrist restraints, if patients are awake, as is often desirable, they may be able to move a tube they want to disconnect toward the tied hand rather than the hand to the tube. Often this is done in a state of stupor, but any further awakening of the patient can cause extreme anxiety with the realization that they are tied to a bed. Elbow immobilizers or arm boards are also employed, but awake patients may be able to disconnect themselves from such restraints. The best restraints are completely ineffective if an awake or semi-awake patient is able to disconnect them. Other problems with these types of restraints include obscuring of potential IV sites, obstruction of full arm skin assessment, joint fixation, and nerve palsies. Creation or worsening of pressure sores, which accounts for significant morbidity in the intensive care patient given that merely edema without device contact can cause skin tears, is also a concern with any device that has continued contact with a patient's skin. Difficulties with existing systems can burden ICU staff, who may be required to spend more time watching one patient to the detriment of another and to their documentation and medication dispersion duties.

SUMMARY OF THE DISCLOSURE

Disclosed embodiments help to prevent self-extubation of nasal or oral tubes and reduce the risk of removal of other indwelling lines and catheters of an awake or semi-awake patient who may reflexively attempt removal of such and allow the early mobilization and exercise necessary for preservation of as much muscle strength as possible, promotion of diaphragmatic motion necessary for liberation from a ventilator, and reduction of patient stress with multiple levels of restraint in between tied and untied, allowing for sedation minimization and improved cognition leading to reduction of the debilitating post-intensive care syndrome (PICS) and complying with a minimum restraint necessary nationwide mandate while simultaneously minimizing dangerous skin contact and allowing full arm skin assessment and usage.

In one implementation, the present disclosure is directed to a medical protective and exercise restraint system. The system includes a rigid restraining structure configured and dimensioned with a length sufficient to extend from a patient's hand to the patient's shoulder with the patient's elbow unbent; a hand strap attached to the restraining structure adjacent the patient's restrained hand, configured to be wrapped around the patient's hand or wrist; and a shoulder strap attached to the restraining structure adjacent the patient's shoulder, configured to be wrapped around the patient's upper arm or axilla, wherein the hand strap and shoulder strap constrict movement of the patient's arm such that the patient is unable to touch the restrained hand to their face. Attachments of the rigid restraining structure to the patient consist of the shoulder strap and the hand strap with or without a thumb strap attached to the restraining structure adjacent the patient's hand, wherein the thumb strap is configured and dimensioned to attach to the hand strap along the volar aspect of the patient's wrist or hand, such that the patient's arm is not contacted by the system between the hand and shoulder straps. The rigid restraining structure is configured to bear against the patient only at two locations; a first location from the bicep to the shoulder and a second location at the hand. The first location is at the shoulder and the second location formed by a graspable member at the palm.

In another implementation, the present disclosure is directed to a method of using a medical protective and exercise restraint system including a rigid restraining structure, a hand strap attached to the restraining structure, and a shoulder strap attached to the restraining structure. The method includes wrapping the hand strap around a patient's hand or wrist, wrapping the shoulder strap around the patient's arm or axilla, and positioning the restraining structure along the patient's arm such that the restraining structure extends from the patient's hand to above the patient's shoulder, the restraining structure does not contact the patient, and the patient is unable to touch their hand to their face.

These and other aspects and features of non-limiting embodiments of the present invention will become apparent to those skilled in the art upon review of the following description of specific non-limiting embodiments of the invention in conjunction with the accompanying drawings.

DESCRIPTION OF DRAWINGS

For the purpose of illustrating the disclosed embodiments, the drawings show aspects thereof. However, it should be understood that the present disclosure is not limited to the precise arrangements and instrumentalities shown in the drawings, wherein.

DETAILED DESCRIPTION

Embodiments disclosed herein offer selectable levels of protective restraint, from liberal to intermediate exercise to strict, thereby allowing for minimal restraint necessary at each patient stage while limiting the range of flexion at the elbow and preventing disconnection of tubes or lines near the face and torso or removal of the disclosed device by a patient. This disclosure includes dual slat embodiments (see, e.g., FIGS. 1A, 1B, and 5) configured to avoid trauma to the skin of the underside of the arm or back of the hand in at-risk patients, such as from skin breakdown when used for typical lengths of time required for intubated patients, by providing minimal skin contact with the arm and hand. Also disclosed are single slat embodiments (see, e.g., FIGS. 2A, 2B, 6, 7A, and 7B) with minimal skin contact at the back of the hand and the side of the torso. Lastly, lateral rod embodiments are disclosed (see, e.g., FIGS. 7A and 7B) with negligible contact with either the arm, hand or the torso as might occur with an underside or a medial portion of an embodiment.

Embodiments disclosed include hand guard systems (see, e.g., FIGS. 1A-8B), which are secured in such a way as to disallow self-removal while providing access to the back of the hand and refraining from circumferential banding. Embodiments of the disclosed hand guard systems provide continual and instant nursing access to arm, wrist and back of hand intravenous or intra-arterial lines, skin assessment and nailbed circulation assessment.

Embodiments of systems disclosed may accommodate either radial or biceps blood pressure cuffs and may include one or more of the following features or configurations: (1) may be untied from the bed or chair for maximal movement with adequate restraint and convertible to a rigid restraint by tying to the bed or chair, further limiting movement of the arm if necessary; (2) may be attached to a bed or chair with an attached resistance band to promote exercise, whether patient-intended or not, and/or provide an intermediate level of restraint for when neither rigid tying nor untying are appropriate; may include a squeezable exercise palm rest and hand guard for further exercise even when rigidly tied which can be removed when hand dexterity is required; (3) and/or may be utilized with most child to adult and bariatric arm sizes. Disclosed systems allow for enhanced patient participation in early mobilization, potentially reduced sedation thereby reducing the risk of delirium while helping to assure that the then awake patient cannot disengage the device, increased thoracic exercise for diaphragmatic strength and secretion clearance thereby hastening recovery from a ventilator and minimize pressure sores and skin breakdown, improved patient communication both with staff for vital symptomatic alerts, with therapists for manual dexterity and writing, and with family and spiritual leaders for spiritual and emotional health, all in a manner which reduces staff monitoring requirements for prevention of self-extubation. Disclosed embodiments may be made from conventional and readily available, medically-approved materials such as plastics, which are latex-free, MRI and other diagnostic imaging-friendly, optionally disposable, lightweight, comfortable, quickly and easily attachable and detachable, sturdy, padded, and cleanable.

Protective and exercise restraint system made in accordance with the teachings of the present disclosure may include one or more length-adjustable slats or rods (generally, any suitable slat, rod, or other-shaped component may be used with any one or more of the systems disclosed herein) with a triceps cradle or triceps strap configured to sit at the axilla and a detachable hand guard system comprising an ergonomic, skin-friendly squeezable palm rest that toggles or otherwise allows comfort and joint-protective motion of the wrist. However, the arrangement prevents patient removal of the device or of the same device on the opposite arm and prevents placement of the hand near a face or of the face near a hand to remove a tube. While primarily described herein in the context of intubated patients, persons of ordinary skill in the art will appreciate that disclosed embodiments are equally applicable for protection of patients who are intubated or otherwise invasively connected to medical support or diagnostic devices.

Dual slat embodiments also may have a forearm cradle and facilitate full-skin assessment and reduction of pressure sores when compared to an arm board style device. An adjustable hook and loop (e.g., Velcro™) strap may be arranged onto a hand guard system in such a way as to render the wrist available for an arterial line, the back of the hand for IV lines, and the forearm for a radial blood pressure cuff, while disallowing patient removal and refraining from circumferential banding of superficial arteries. A second adjustable hook and loop strap at the upper biceps/axilla, which may attach to the triceps cradle, may secure the upper arm in the device while allowing room for a biceps blood pressure cuff. An optional, movable, contact-free protective curved strap can be positioned over a desired site on the arm. The hand guard or palm rest may be removable for purposes of more complex patient tasks such as hand communication. A moderate resistance band with bed connector may be attached to the distal end of the slat to provide intermediate flexible restraint protection as well as exercise while an inflexible tie may be attached to the distal end of the slat to provide strict restraint protection. Different strength resistance bands may be exchanged if more intense exercise or an additional intermediate level of restraint is desired. Non-use of the straps provides minimal restraint protection while still providing protection from self-extubation. Different institutions have different policies and definitions of a restraint and levels of restraint such that non-use of straps may not be considered a restraint in some instances. Institutions also may have different materials standards, and embodiments of the disclosed devices are readily adapted to the use of different materials.

Figure 1A:
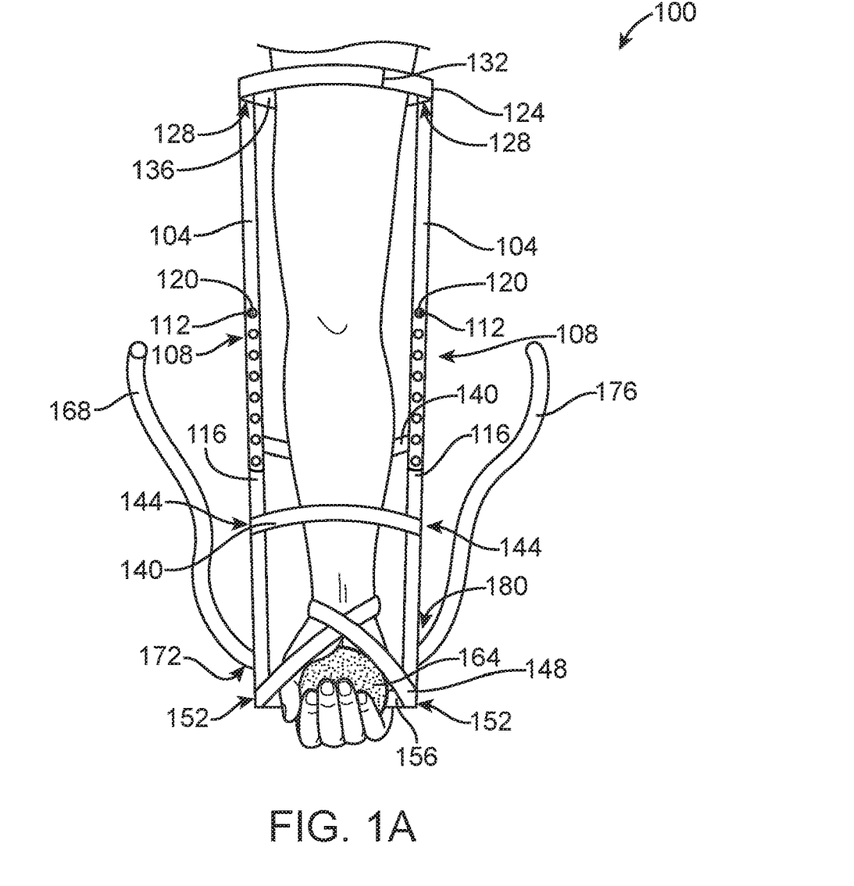
FIG. 1A is a schematic diagram of an exemplary protective and exercise restraint system illustrating a top view of a dual slat embodiment.
Figure 1B:
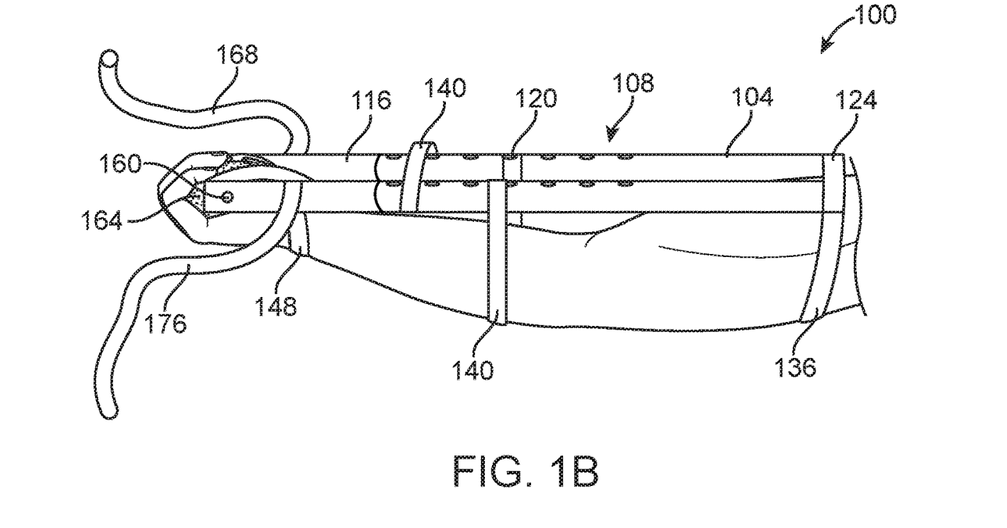
FIG. 1B is a schematic diagram of an exemplary protective and exercise restraint system illustrating a side view of the dual slat embodiment of FIG. 1A.
Figure 5:
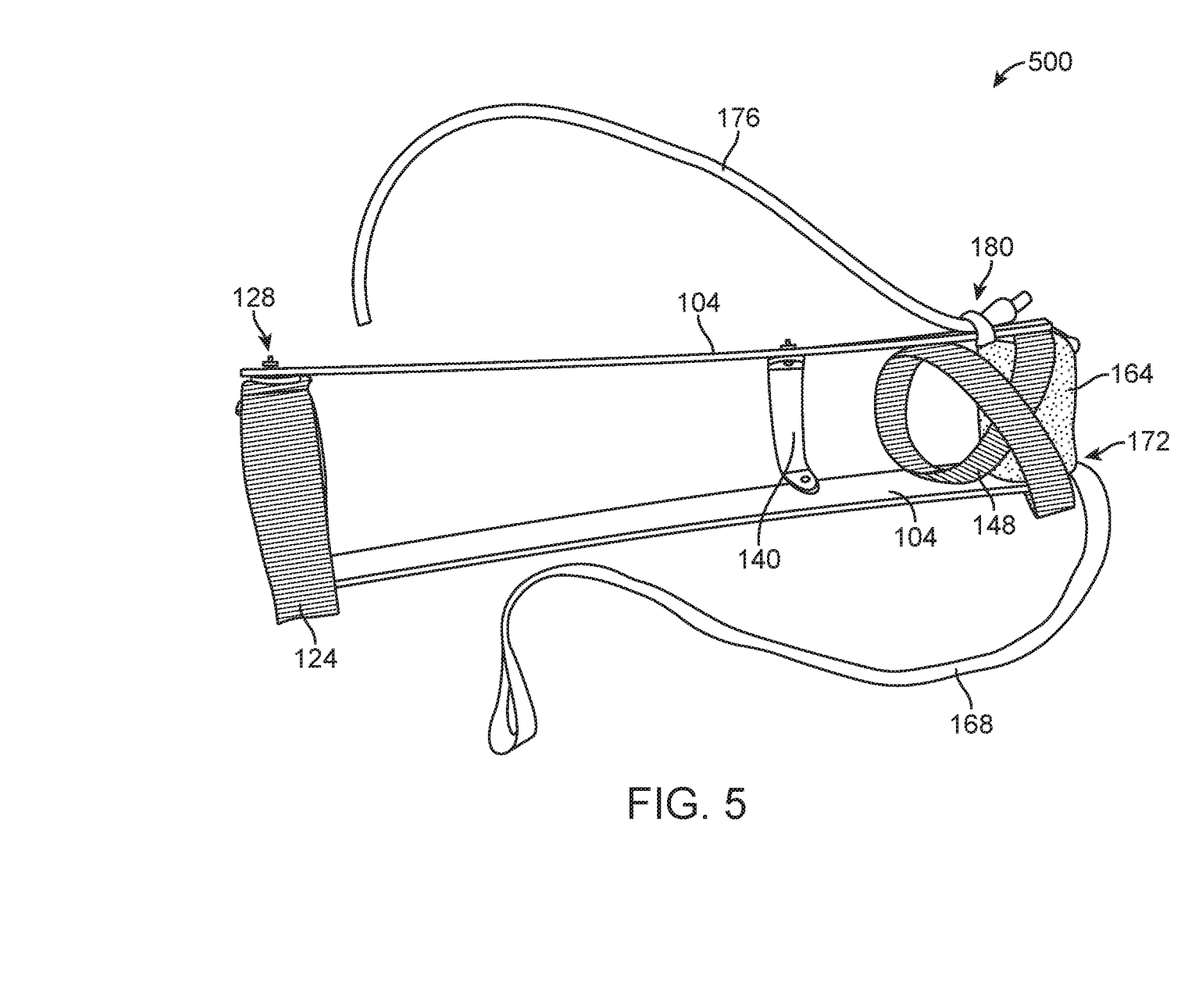
FIG. 5 is a schematic diagram of a dual slat embodiment of a protective and exercise restraint system made in accordance with the present disclosure.

Turning now to the drawings, FIGS. 1A and 1B illustrate a dual slat protective and exercise restraint system 100. As shown, two optionally extendable slats 104 are arranged on either side of a patient's arm. Extension of slats 104 may be implemented by using a telescoping mechanism 108 that can be locked by aligning a spring-loaded ball-bearing 112 disposed in an optional slat extension 116 with one of two or more holes 120 disposed in the slats or by using any other appropriate mechanism. In order to affix system 100 to a patient, two or more straps can be used. As shown in FIGS. 1A and 1B, a bicep strap 124 may be attached at proximal ends 128 of slats 104. In some embodiments, bicep strap 124 may be inelastic, elastic, and/or composed of two straps that can be attached to one another using a hook and loop fastener 132 or other appropriate type of fastener. System 100 may further include a tricep strap 136, which, like bicep strap 124, may be inelastic, elastic, and/or composed of two straps that can be attached to one another using a hook and loop fastener 132 or other appropriate type of fastener. Optional forearm straps 140 may be attached to slats 104 and/or slat extensions 116, as appropriate, using any desired attachment mechanism, such as hook-and-loop fasteners 144. Forearm straps 140, like bicep strap 124 and tricep strap 136, may be inelastic, elastic, and/or composed of two straps that can be attached to one another using a hook and loop fastener 132 or other appropriate type of fastener. The patient's hand may be restrained using a hand strap 148, which may be connected to slats 104 and/or slat extensions 116 and/or hand guard 156, as appropriate, using any desired attachment mechanism, such as hook-and-loop fasteners 152 or tunneled slots. A hand guard 156 may be disposed between slats 104 and/or slat extensions 116, as appropriate, using any desired attachment mechanism (e.g., bolts 160), may be telescoping, and a detachable, optional squeezable palm rest 164 may be disposed on or around, hook and loop fastened to, molded with, adhered to, or otherwise arranged such that a patient can grip the palm rest during use without necessarily having to touch the hand guard itself, which may consist of harder materials than the palm rest. A resistance band 168 may be attached to one or more of slats 104 and/or slat extensions 116, as appropriate, at a resistance band attachment point 172, and an inflexible tie 176 may be attached to one or more of the slats and/or slat extensions, as appropriate, at an inflexible tie attachment point 180. An alternative dual slat protective and exercise restraint system 500 is shown in FIG. 5 with only one forearm strap 140. Although inflexible tie 176 is shown as being tied to slat 104 in FIG. 5, any suitable connection may be used. Further, although a loop of material is shown at the end of resistance band 168 in FIG. 5, this is only one example of a suitable connector that would enable connection to a suitable complementary apparatus (e.g., a security cable or locking clasp) attached to a bed, chair, or other nearby structure. Rather than or in addition to a loop, any other suitable connection means can be used with resistance band 168 and/or inflexible tie 176. Further still, although various attachments in FIG. 5 are illustrated as nut and bolt connections, other types of connections could be used, such as hook and loop connections, buttons, or otherwise.

Figure 2A:
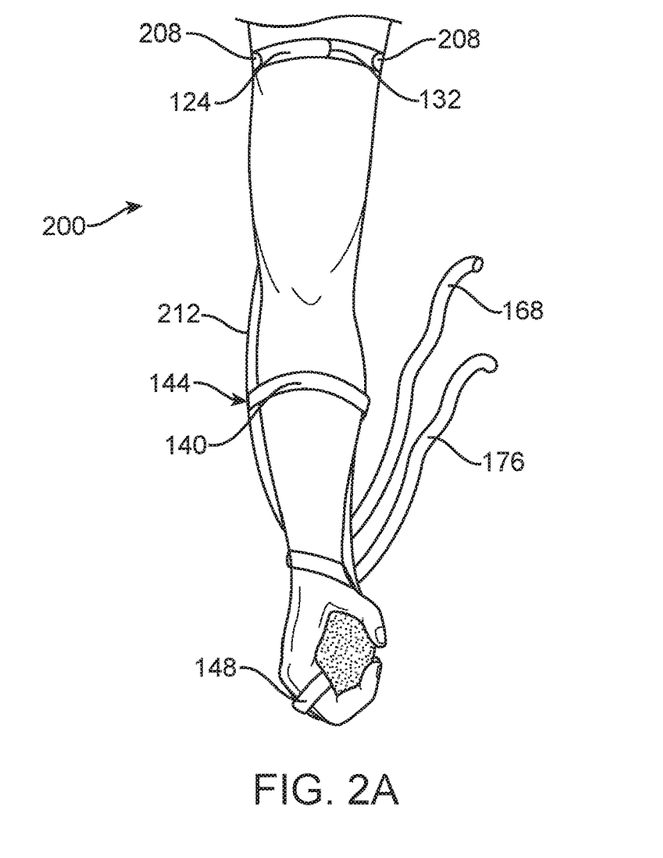
FIG. 2A is a schematic diagram of an exemplary protective and exercise restraint system illustrating a top view of a single slat embodiment.
Figure 2B:
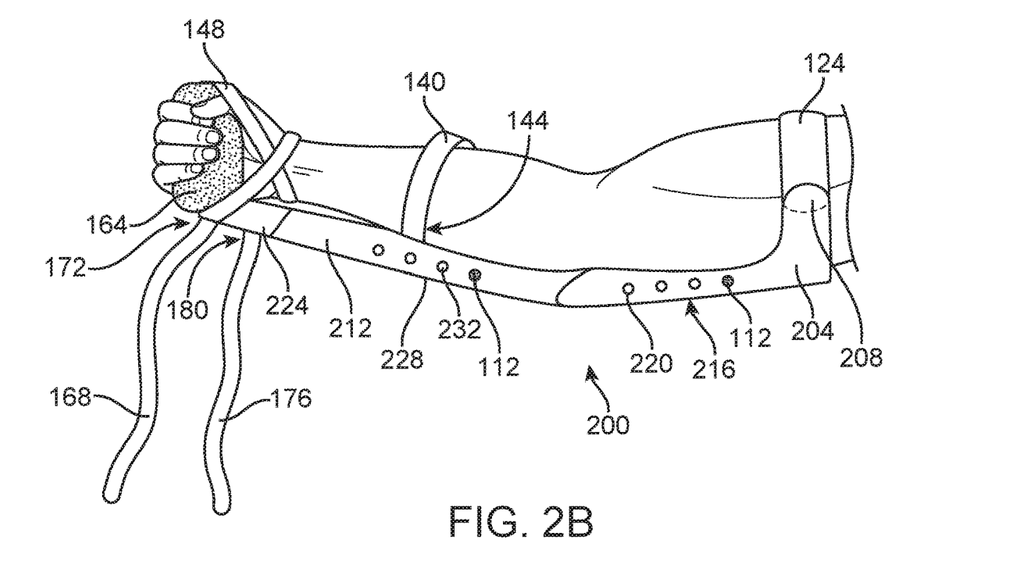
FIG. 2B is a schematic diagram of an exemplary protective and exercise restraint system illustrating a side view of the single slat embodiment of FIG. 2A.
Figure 6:
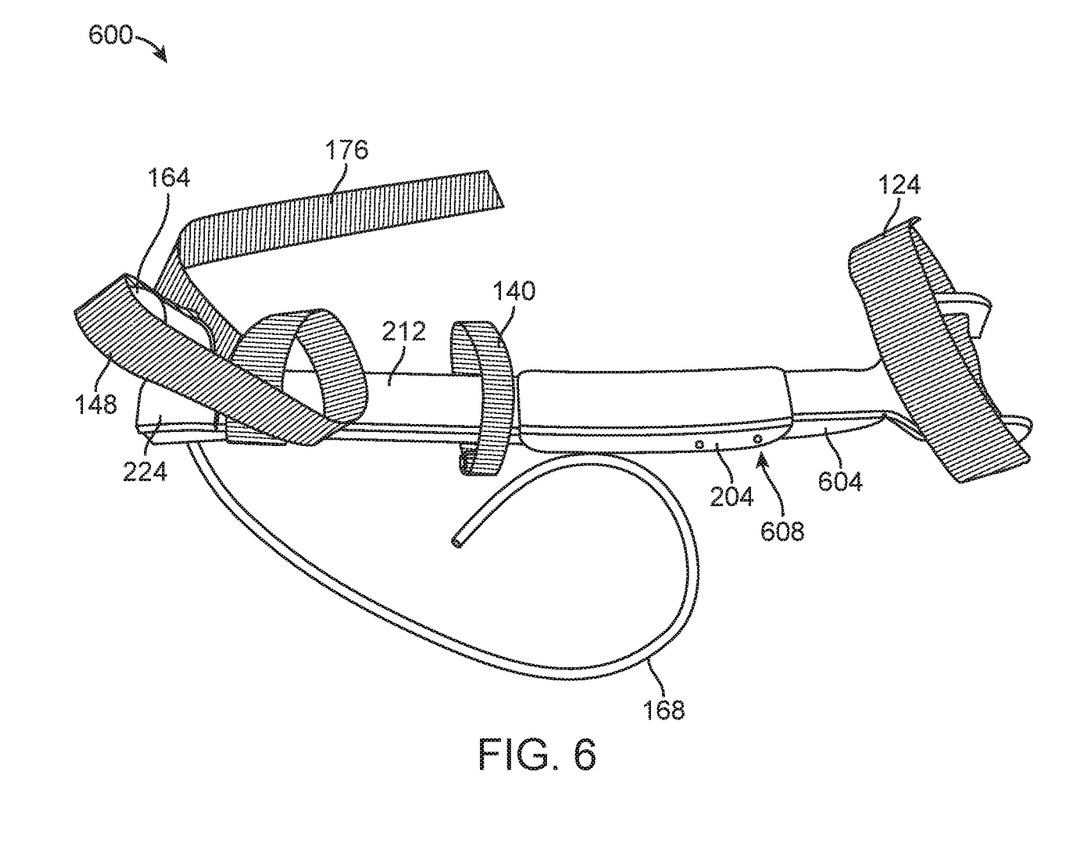
FIG. 6 is a schematic diagram of a single slat embodiment of a protective and exercise restraint system made in accordance with the present disclosure.

FIGS. 2A and 2B illustrate a single slat protective and exercise restraint system 200. Portions of system 200 that can be implemented using parts similar or identical to those of system 100 use the same reference numerals as are used in connection with FIGS. 1A and 1B and will not be further described in descriptions of subsequent embodiments, as the subsequent description of FIGS. 2A and 2B and other embodiments will focus on aspects of system 200 that differ from system 100. As shown in FIGS. 2A and 2B, single slat protective and exercise restraint system 200 may include many of the same components as system 100, but may be implemented in a single slat and/or dorsal arm rest fashion. As best seen in FIG. 2B, bicep strap 124 may be connected to a tricep cradle 204 at tricep cradle connecting regions 208 using appropriate attachment means, such as an adhesive and/or hook and loop fasteners. A tricep cradle extension 212 may be connected to tricep cradle 204 through a telescoping mechanism 216 that can be locked by aligning a spring-loaded ball-bearing 112 disposed in the tricep cradle extension with one of two or more holes 220 disposed in the tricep cradle or by using any other appropriate mechanism. Similarly, a hand guard 224 may be connected to tricep cradle extension 212 through a telescoping mechanism 228 that can be locked by aligning a spring-loaded ball-bearing 112 disposed in the hand guard with one of two or more holes 232 disposed in the tricep cradle extension or by using any other appropriate mechanism. An alternative single slat and/or dorsal arm rest protective and exercise restraint system 600 having a slightly different arrangement from system 200 is shown in FIG. 6. As shown, system 600 may include an axilla extension 604 and a telescoping mechanism 608 like those described above that enables the axilla extension to be adjusted relative to tricep cradle 212. In such an implementation, bicep strap 124 may be connected to and/or fed through slots on axilla extension 604. Although not shown in FIG. 6, an inflexible tie like inflexible tie 176 and an attachment point like attachment point 180 may be used with system 600. Generally, any of the systems disclosed herein may be outfitted with inflexible tie 176 and/or resistance band 168, as desired.

Figure 3:
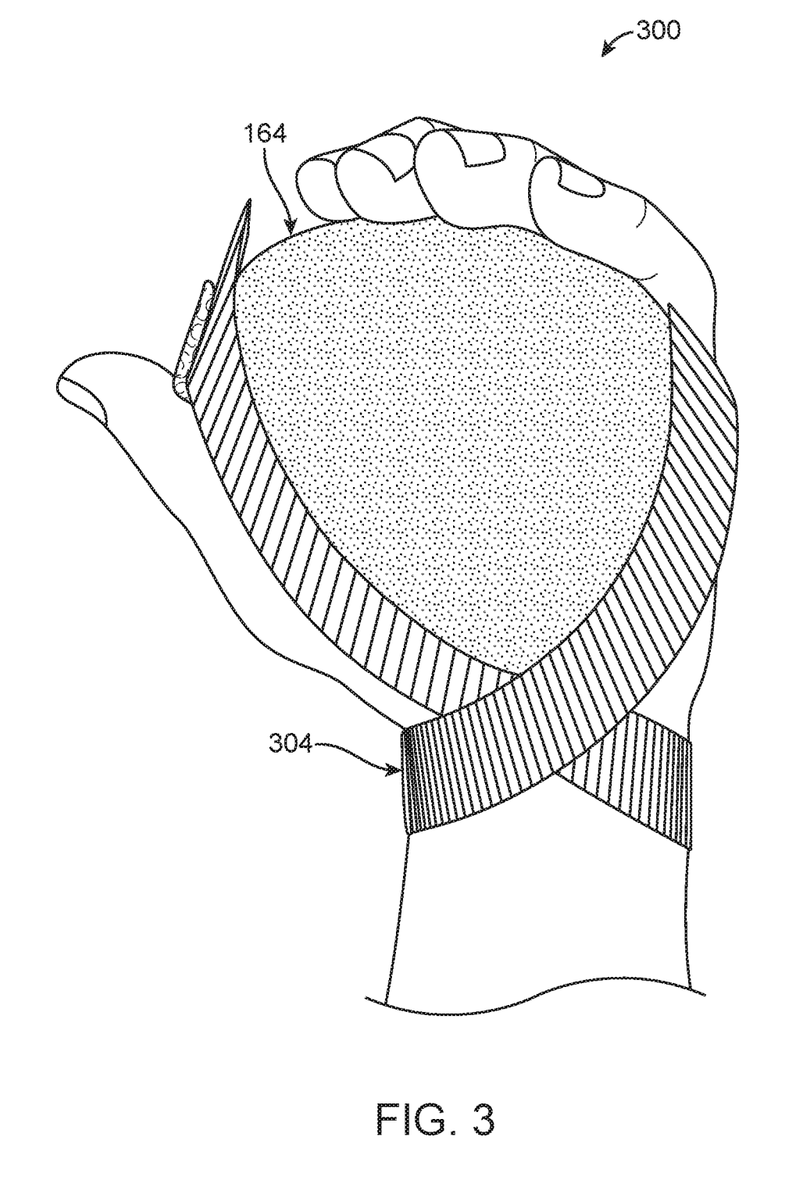
FIG. 3 is a schematic diagram of an exemplary hand-securing component that may be used with any of the protective and exercise restraint systems disclosed herein, as viewed from the volar or palmar side.
Figure 4:
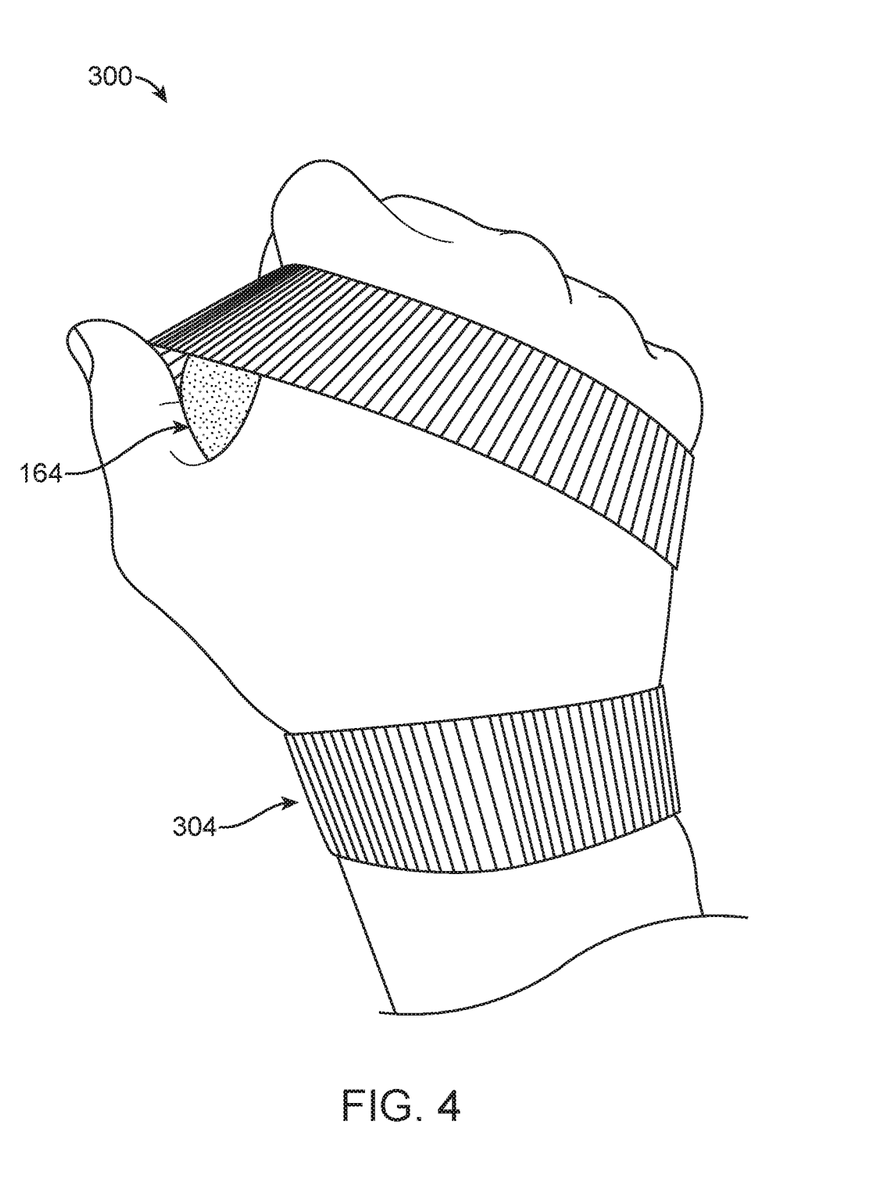
FIG. 4 is a schematic diagram of an exemplary hand-securing component that may be used with any of the protective and exercise restraint systems disclosed herein, as viewed from the dorsal or back of hand side.

FIGS. 3 and 4 illustrate a hand securing component 300, which may be used as part of and/or alongside a hand guard. As shown, hand securing component 300 may include a squeezable palm rest 164 as well as one or more straps 304, which may in some embodiments be the same as hand strap 148. As shown in FIG. 4, one or more straps 304 may wrap around a patient's wrist and/or hand one or more times in such a way as to render the radial artery area unobstructed and non-compressed before being attached to itself and/or a hand guard or palm rest using appropriate means, such as hook and loop fasteners, attachment points and/or tunneled slots.

Figure 7A:
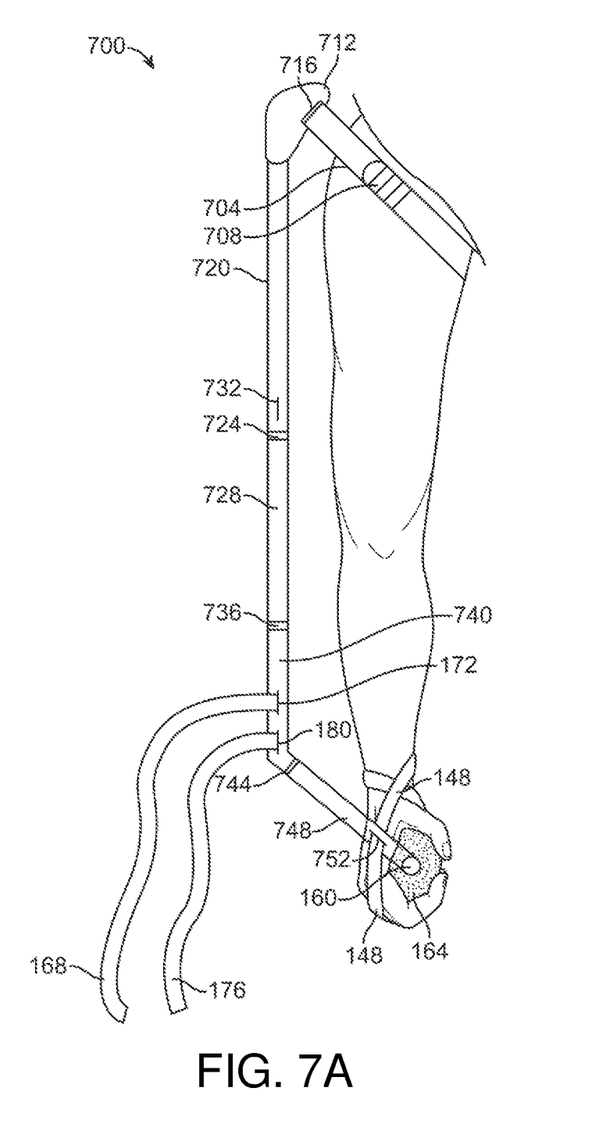
FIG. 7A is a schematic diagram of a single slat embodiment of a protective and exercise restraint system made in accordance with the present disclosure.

FIG. 7A illustrates a single slat lateral rod protective and exercise restraint system 700. As shown, system 700 may include a shoulder strap 704, which may be inelastic, elastic, and/or composed of two straps that can be attached to one another using a hook and loop fastener 708 or other appropriate type of fastener. Shoulder strap 704 may be attached to a shoulder connector 712 via one or more slots 716 and/or other mechanisms, and the shoulder connector may be mounted to an optionally extendable rod 720 which may curve about the shoulder. The extent of rod 720 from the strap connector to the straight portion of the rod may be encased in a thick cushioned sheath. Extension of rod 720 may be implemented by using a telescoping mechanism 724 in the straight portion of the rod that can be locked in place by aligning a spring-loaded ball-bearing disposed in an optional rod extension 728 with one of two or more holes disposed in the rod or by using any other appropriate mechanism. In some embodiments, a flip lock 732 or other type of locking mechanism may be provided separately or as a part of telescoping mechanism 724. Rod extension may be rotatably connected via rod connector 736 to a forearm brace 740, and resistance band 168 and inflexible tie 176 may be connected to the forearm brace via attachment points 172 and 180, which may be implemented as slots, hook and loop fasteners, or otherwise as appropriate. In some embodiments, resistance band 168 and/or inflexible tie 176 may include attachment components (e.g., slots, hook and loop fasteners, buttons, or otherwise as appropriate) that can be secured to a patient's bed or chair or other nearby and at least similarly relatively immobile structure. Forearm brace 740 may be rotatably connected via a wrist pivot connector 744 to a wrist brace 748, and the wrist brace may include one or more slots 752 or other mechanism(s) suitable for securing hand strap 148 to the wrist brace. Although wrist strap 148 is shown in FIG. 7A as having a cross-over point near the anatomical snuff box, the cross-over point may instead be located at the front of the volar aspect of the wrist, i.e., along the right side of the wrist shown in FIG. 7A. Further, in some embodiments, wrist strap 148 may connect to bolt 160 or squeezable palm rest 164 and/or a support structure therefor using appropriate connection means rather than or in addition to extending through slot 752. In some embodiments, a hand guard, squeezable palm rest, and/or other components located near the hand of systems disclosed herein may be detachable and/or rotatable such that the hand-related components of a system like system 700 can be removed or rotated, the remainder of the device flipped over along its longitudinal axis, and the hand-related components reattached if they were removed instead of being rotated, such that a system like system 700 can be adapted for use with a right arm or left arm.

In some embodiments where both arms of a patient are protected with systems disclosed herein, one or more protective chest straps and/or back straps (not shown) may cross in front of (e.g., across or adjacent the nipples) and/or behind the patient to constrict relative movement of the two systems. In some embodiments, the chest and/or back straps may extend across the torso parallel to one another; however, one or more of the chest and/or back straps may additionally or alternatively be configured to cross one another, where necessary and/or appropriate. For example, when two systems like system 700 are used to protect a patient, a chest strap may join the systems through attachment to a shoulder strap like shoulder strap 704 of each system (left and right arms). In some embodiments, a shoulder or back strap may comprise hook and loop material, buttons, or other connection devices such that the chest or back strap can be connected to a shoulder strap like shoulder strap 704 or any other appropriate portion of one or more of the systems disclosed herein. In some embodiments, chest and/or back straps may be permanently affixed to one or more of the systems disclosed herein such that the systems can be attached to each other using one or more of the chest and/or back straps, e.g., using hook and loop or other appropriate fasteners to connect chest straps together and/or back straps together. It may be preferable with some embodiments and/or certain patients not to utilize a back strap as described above because it may contribute to creation of pressure sores and may not help to prevent the restraint from rolling under the back of the patient.

In some embodiments, shoulder connector 712, rod 720, rod extension 728, forearm brace 740, and/or wrist brace 748 may comprise a single restraining structure, such as a rod, bar, or slat, which may curve and slope medially and downward from the forearm brace portion of the structure toward the wrist brace portion of the structure such that the forearm brace portion of the structure may be inches higher than and lateral to the outermost portions of a patient's arm. That is, with a patient's arm having system 700 attached thereto and resting on a surface as shown in FIG. 7A, wrist brace 748 or a wrist brace portion of a structure made in accordance with an embodiment that combines one or more of rod 720, rod extension 728, forearm brace 740, and/or wrist brace 748 into a single structure, may be rigid and may extend vertically and laterally away from the patient's hand and squeezable palm rest 164 (e.g., such that at least half of the structure is positioned vertically above a horizontal plane passing through the patient's arm). In some embodiments, rod 720, forearm brace 740, and/or wrist brace 748 may comprise and/or be enclosed by a thin or thick padded sheath, as may any one or more of the other components described in this disclosure. In some embodiments, rod 720, or a structure made in accordance with an embodiment that combines one or more of rod 720, rod extension 728, forearm brace 740, and/or wrist brace 748 into a single structure, may curve laterally around the patient's shoulder such that shoulder strap 704 may extend across the clavicle, optionally forming a right angle with at least one surface of the clavicle. In some embodiments, such a structure or combination of components may only curve away from the wrist as described above with the remainder of the structure or combination of components forming a substantially straight or slightly curved line (optionally similarly to a windsurfing boom, and optionally crossing the shoulder or bending around the shoulder relative to a front view of the patient).

Figure 7B:
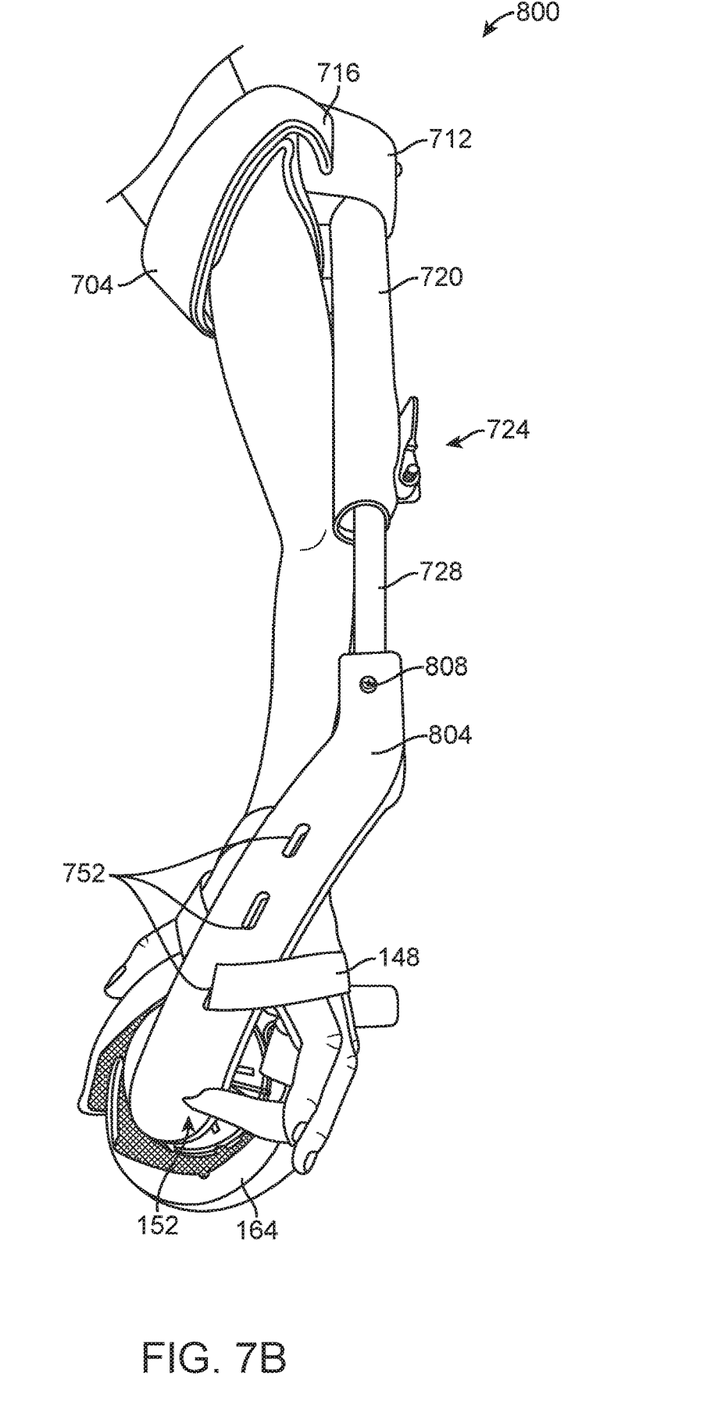
FIG. 7B is a schematic drawing of a prototype embodiment of a single slat protective and exercise restraint system made in accordance with the present disclosure.
Figure 7C:
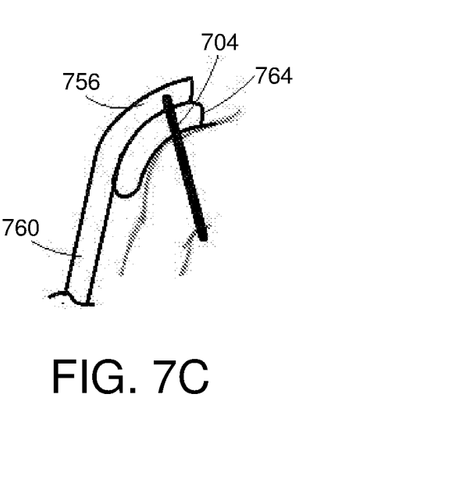
FIG. 7C is a schematic detail of an upper end portion of a further alternative embodiment.

As shown in FIG. 7C, an alternative shoulder connector 756 functionally similar to shoulder connector 712, and an alternative rod 760 like rod 720, may comprise a single piece of material. Shoulder strap 704 may be connected to an upper end of alternative shoulder connector 756 using suitable connection means (e.g., a slot and/or hook and loop fastener) such that the shoulder strap may extend across the clavicle, optionally forming a right angle with at least one surface of the clavicle. As also shown in FIG. 7C, a shoulder pad 764 may be affixed to, built into, or otherwise associated with alternative shoulder connecter 756 to prevent the alternative shoulder connector from directly abutting the patient's skin, getting lodged under the patient's shoulder, or, in some cases, riding up on top of the patient's shoulder, although in other cases the connector may be allowed to ride up on top of the patient's shoulder (depending on the patient's condition). Shoulder pad 764 may comprise any suitable material and may have any appropriate shape, optionally either contoured to the patient's shoulder or simply a cylindrical pad surrounding alternative shoulder connector 756, provided that it prevents the alternative shoulder connector from directly abutting the patient's skin, getting lodged under the patient's shoulder, or, in some cases, as noted above, riding up on top of the patient's shoulder. Although shoulder pad 764 is shown in FIG. 7C attached to alternative shoulder connector 756, it may be used with other components and/or devices disclosed herein, such as rod 720, shoulder connector 712, slats 104, and/or tricep cradle 204, among others. Shoulder pad 764 is preferably configured so that it will not be in contact with or press against the patient's skin, unless the patient strains against it or otherwise moves so that the shoulder pad is forced into contact with the skin despite being initially attached in such a way that it does not touch the skin. In some embodiments, shoulder pad 764 may be arranged such that it is separated from a patient's skin by one inch, give or take a centimeter, when the patient is at rest. In some embodiments, systems disclosed herein may also be arranged such that no component of the system comes within one inch, give or take a centimeter, from the patient's bed, chair, or other support structure when the patient is at rest. In some embodiments, all of the straps used to connect a system implemented in accordance with the present disclosure should only be loosely connected to the patient so as to allow underneath it the insertion of one to two fingers to prevent unnecessary pressure sores; however, with some patients, it may be necessary to tighten the straps in order to prevent the patient from removing the system or otherwise circumventing one or more of its protective functions. Generally, systems disclosed herein may be arranged such that only a wrist strap or hand strap system and shoulder strap touch a patient's skin after being arranged properly on the patient while the patient is at rest.

FIG. 7B illustrates a single slat or lateral rod protective and exercise restraint system 800 similar to system 700. As shown, system 800 omits various elements of system 700 and provides sturdier, nonrotatable connections, which may be appropriate under certain conditions. In system 800, like in system 700, extendable rod 720 and optional rod extension 728 are joined with a telescoping mechanism 724. However, unlike system 700, in system 800, rod extension 728 is connected directly to a nonrotatable wrist brace 804 (e.g., using bolt 808 or other appropriate connector), which may include one or more slots 752 enabling connection of hand strap 148 at one or more locations along the nonrotatable wrist brace. Similarly, slots 752 enable connection of a resistance band and/or inflexible tie, as desired, at one or more locations along nonrotatable wrist brace 804. More or fewer slots may be used and/or different connection means may be used, such as hook and loop connectors or others known in the art. In some embodiments, hand strap 148 may connect to squeezable palm rest 164 or a support structure thereof, which may be identical or similar to hand guard 156 of FIG. 1A.

Although relatively wide straps are shown in FIG. 7B, thinner straps may be used, as appropriate. Generally, under ideal conditions, a system like system 700 or system 800 should only touch a patient's skin intermittently at a minimal number of points, such as at the locations of one or more loose straps so as to allow underneath it the insertion of one to two fingers, while other portions of the system, such as rod 720, rod extension 728, forearm brace 740, wrist brace 748, and/or nonrotatable wrist brace 804, should be arranged such that they do not touch the patient's skin.

Figure 8A:
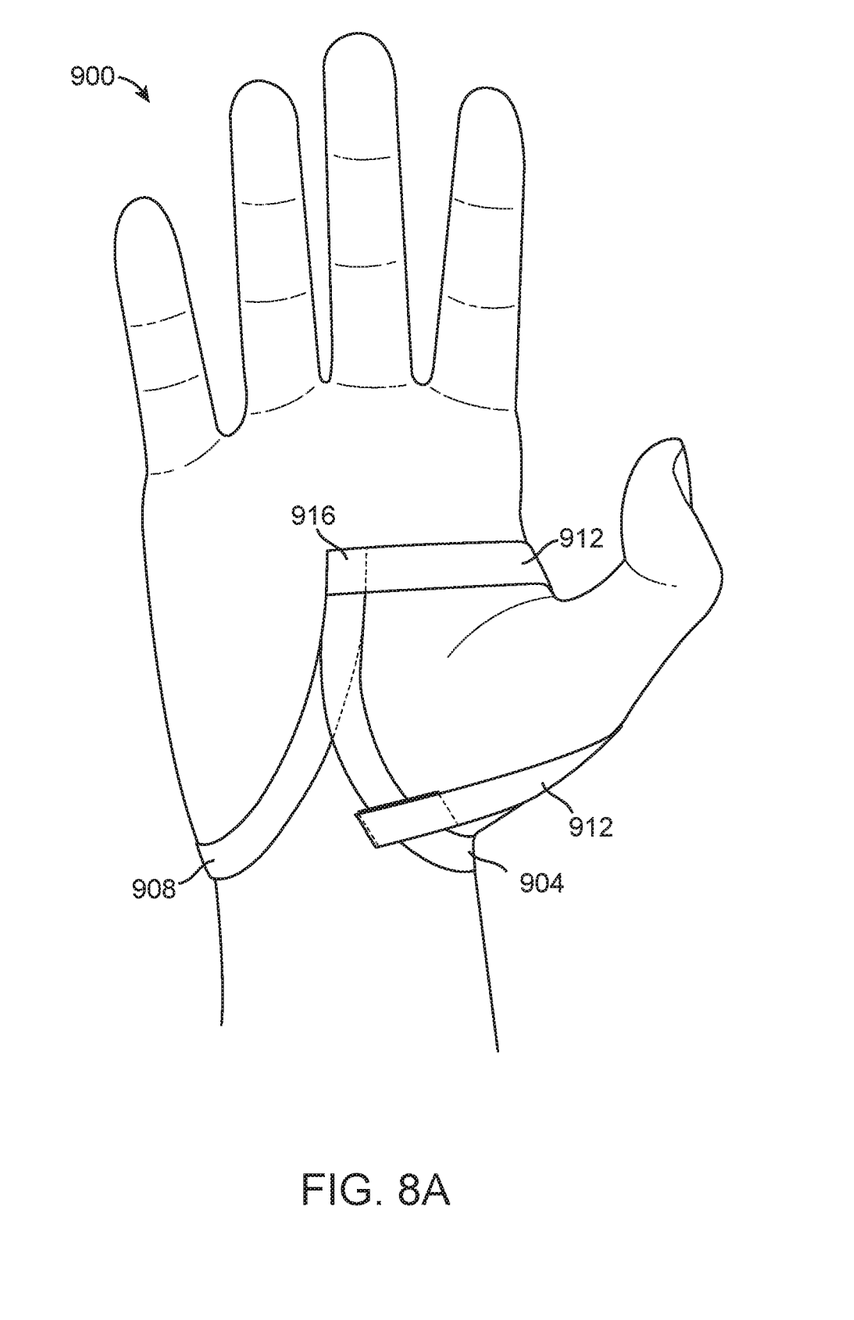
FIGS. 8A and 8B are schematic diagrams of a hand strap system made in accordance with the present disclosure.
Figure 8B:
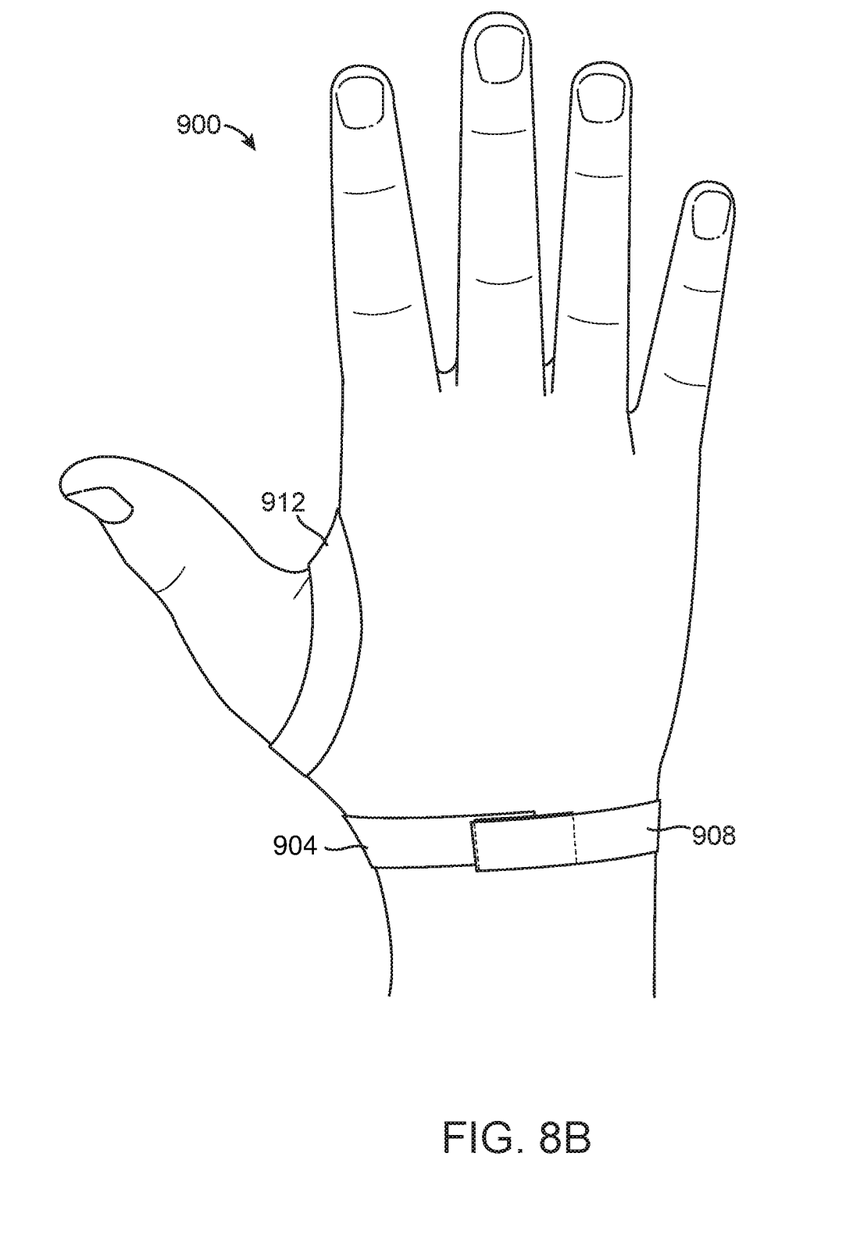

FIGS. 8A and 8B illustrate a hand strap system 900 that can be used with one or more of the other systems disclosed herein. Hand strap system 900 may include three straps, although in some embodiments these straps may be manufactured as a single, tripartite strap. As shown in FIG. 8A, a first wrist (or hand) strap 904, a second wrist (or hand) strap 908, and a thumb strap 912 may extend from a connection point 916, which may comprise a grommet or other connection element suitable for connection to a hand guard, wrist brace, or other suitable component of one or more of the other systems disclosed herein. In some embodiments, more than one connection point may be used, such that first and second wrist straps 904, 908 connect to a first connection point and thumb strap 912 connects to a second connection point. Further, in some embodiments, first wrist strap 904, second wrist strap 908, and thumb strap 912 may all connect to their own connection points on one or more portions of the other systems disclosed herein. As shown in FIG. 8B, in some embodiments, first and second wrist straps 904, 908 may be affixed to one another behind the wrist using hook and loop fasteners, although any suitable connection may be used. In some embodiments, first and second wrist straps 904, 908 may be implemented as a single, optionally slightly elastic strap (such that the strap can be placed around the patient's hand but static enough that none of the protective functions of the overall system with which it is used are compromised). As shown in FIGS. 8A and 8B, thumb strap 912 may be wrapped around the patient's thumb and attached to first wrist strap 904 between the lateral aspect of the wrist and a connection point for attaching the first wrist strap to a component of one or more of the other systems disclosed herein, such as connection point 916. Generally, thumb strap 912 may be attached to first wrist strap 904 anywhere along the volar aspect of the wrist or hand with a hook and loop connection or other suitable connection.

In some embodiments, a hand guard of a sturdy material may attach to a wrist brace portion, a rod, forearm brace, and/or a slat like one or more of those disclosed herein. The hand guard may contain one or more attachment points at its volar surface for one or more wrist straps like first and second wrist straps 904, 908 and thumb strap 912, which may comprise hook and loop material. The medial wrist strap may course cephalad and medially while the lateral wrist strap may course cephalad and laterally, each to loosely attach, so as to allow underneath it the insertion of one finger, to each other by hook and loop or other mechanism at the dorsal aspect of the wrist. Thumb strap 912 may course from the volar aspect of the hand guard across the anatomical snuff box toward the posterior aspect of the thumb, then toward the anterior thenar eminence, and loosely attach, so as to allow underneath it the insertion of one finger, to the lateral wrist strap by hook and loop or other mechanism. The hand guard may optionally be covered by a detachable squeezable ovoid palm rest poised to render the hand and wrist in a non-stressed position using hook and loop or other means of detachably fastening to the hand guard while not obstructing the wrist and thumb straps or their attachment points.

A loose shoulder strap allowing the insertion underneath same of one to two fingers like shoulder strap 704 and a restraining structure comprising, e.g., shoulder connector 712, rod 720, rod extension 728, forearm brace 740, and/or wrist brace 748, or a single restraining structure, such as a rod, bar, or slat that does not touch the arm may allow enough elbow movement that a patient will not endure any joint damage from heterotopic ossification or contractures while also guarding against nerve palsies at the shoulder area and disallowing self-extubation as well as providing full skin access. One or more loose straps at the hand allowing insertion underneath same of one finger, such as straps 904, 908, and 912, may allow enough movement at the wrist and fingers for the same reasons while disallowing device removal. Skin can be torn as a result of edema without anything resting on the skin, and minimal contact between devices disclosed herein and a patient's skin is very important. The shape of a restraining structure like that shown in FIG. 7A curving laterally and upward relative to a patient's hand and/or arm may allow a hand to swell without meeting the resistance of a hard component of device (e.g., wrist brace 748). The position of a restraining structure like that shown in FIG. 7A being higher than the arm when the patient is lying at rest on a bed with their arms at their sides allows the arm to bend without having constant contact with the device. Padding at the shoulder, such as shoulder pad 764, allows the device to be far enough away from the arm, even in a bariatric patient, that skin contact can still be minimized. A thin padded sheath around the major components of the device (e.g., shoulder connector 712, rod 720, rod extension 728, forearm brace 740, and/or wrist brace 748, or a single restraining structure, such as a rod, bar, or slat) may protect the patient from any intermittent contact with the device and may protect staff who might be hit with the device from injury. An optional chest strap may help position the device to prevent it from making its way to the underside of the supine patient. Although a back strap may be contraindicated for reasons stated above, i.e., to avoid skin pressure and keep the restraining structure away from the underside of the patient, a back strap may nonetheless be used where the material is thin and/or nonabrasive or where a patient is otherwise able to disengage themselves from the device.

In one example of use of disclosed embodiments, a medical staff person places the patient's arms in protective and exercise restraint systems like those described herein (one per arm) with the palm adjacent the hand guard and touching the squeezable palm rest and the uppermost arm area in a triceps cradle, which may abut the axilla. The biceps strap should be secured so as not to hinder circulation. The hand strap, which may be attached to the hand guard, may then be secured by starting at the base of the $5^{th}$ finger anteriorly toward the area below the thumb (thenar eminence), then around the back of the wrist and onto the hypothenar eminence, then crossing anteriorly in an upward diagonal direction toward the area just above the thumb, where it may then be secured to another point on the hand guard. One or more optional forearm straps may be secured in various positions, assuring clearance of any IVs. Depending on the level of restraint ordered and the desire for movement and exercise, either no bed tie, or the resistance band, the inflexible tie, or both may be attached to the patient's bed or chair. The level of restraint can be easily selected and changed depending upon the patient's changing needs. Whether tied or untied, the patient can neither reach tubes and lines near the torso and face nor remove the device itself. Movement and exercise are encouraged by the resistance band and the squeezable palm rest. After reading this disclosure in its entirety, those of ordinary skill in the art will understand that, although particular uses of particular devices are described in this paragraph and throughout the disclosure, various other similar uses of various other devices taught and disclosed herein may be used.

As may be apparent to persons of ordinary skill, embodiments of the disclosed systems allow for three or more levels of restraint, all of which prevent the awake and so-inclined subject from disengaging from the restraint or approximating the face and hand, including one configuration for resistance exercise therapy. Other advantages of the disclosed systems include providing a safe level of freedom and exercise while preventing self-extubation and self-removal even by the agitated or determined patient, providing continual access to forearm and back of hand intravenous lines and wrist arterial lines and for skin assessment (full visualization of the back of the arm and hand allowed by dual slat and lateral rod models with reduction of pressure ulcers and visualization of the back of the hand with the single slat model) with simultaneous prevention of the agitated patient from disengaging the hand and subsequently the restraint on the opposing arm even while in the untied, more liberal configuration. Disclosed systems also allow movement of fingers and thumbs, rotation of the wrist, a small amount of bending at the elbow, and full range of motion at the shoulder for joint protection.

Embodiments of the systems disclosed are length adjustable and configured to accommodate most arm widths, thereby allowing space for separate radial and biceps blood pressure cuffs in patients who might otherwise not have room. The system may be quickly converted to three or more levels of restraint, and affords 360 degree skin assessment and reduced risk of pressure sores of the underside of the arm or back side of the hand (dual slat and lateral rod models) or of the back of the hand solely (single slat model) or has an exercise modality (resistance band and squeezable palm rest) or quickly and easily interchange between three or more levels of restraint.

Further features of the disclosed systems include: (1) securable at three or more levels of hand and arm restraint (i.e. "secure tri-plus level restraint"); (2) secure tri-plus level hand and arm restraint system with an anxiety-reducing intermediate movement and exercise configuration that allows mobility and resistance exercise therapy at multiple levels which can be utilized when the untied (to the bed or chair) state is too risky and the inflexible tie (to the bed or chair) is too strict or anxiety provoking and/or if the patient can exercise, whether knowingly or unknowingly in order to accommodate the ever-changing needs of the intubated patient promoting minimal levels of both restraint and sedation necessary while disallowing self-removal by the so-intentioned patient; (3) secure tri-plus level hand and arm restraint system with removable exercise hand guard system including squeezable ergonomically-shaped exercise palm rest; (4) hand and arm restraint system with a hand guard that toggles to allow moderate bilateral sideways rotation of the wrist for comfort and joint protection; (5) secure tri-plus level hand and arm restraint system which by its hand guard design disallows self-removal of the fingers and hand by the fully awake and so-intentioned patient for interference with lines and tubes even when not tied to the bed or chair thereby disallowing self-extubation and assuring minimized sedation without fear of disengagement of the device; (6) secure tri-plus level hand and arm restraint system with continual visibility of back of the hand intravenous line sites; (7) secure tri-plus level hand and arm restraint system with lack of circumferential banding and continual visualization of and non-interference with wrist arteries and arterial line sites; (8) secure hand and arm restraint system with minimization of skin contact of the underside of the arm with the dual slat and lateral rod models for non-interference with skin integrity and continual assessment; (9) secure hand and arm restraint system with room for the patient to straighten and bend the arm slightly at will for comfort in the dual slat and lateral rod models; and (10) utilize a strapping technique which is loose and only intermittently makes skin contact to reduce the risk of pressure ulcers and nerve palsies.

Using systems disclosed herein, a single device may be effectively employed for all levels of restraint that may be desired throughout a patient's changing status thereby always promoting minimal restraint necessary. Disclosed systems provide unique features that prevent self-extubation while not strapped to a bed or chair for an awake and at-risk patient who might otherwise wriggle out of a palm strap, and encourage early mobilization and exercise promoting the strength required for advancement from a ventilator. The dual slat and lateral rod embodiments do not obscure the underside of the arm thereby reducing the risk of pressure sores and skin breakdown. Dual slat, single slat and lateral rod embodiments expose the back of the hand for intravenous lines, also optimizing skin integrity in this area. The lateral rod model exposes the back of the hand, underside of the arm and the medial aspect of the arm which abuts the torso. The multiple degrees of increased freedom of movement provided by disclosed systems allow for reduced patient agitation and therefore sedation medication may be decreased and minimized which in turn promotes increased patient cognition and thereby would be more likely to reduce the incidence of delirium and post-intensive care syndrome, a form of PTSD. Once a patient-appropriate restriction configuration is in place, direct nurse or sitter monitoring may not be necessary whereas untying the restraints currently available without constant 1:1 supervision invites self-extubation.

EXPERIMENTAL RESULTS

Prototypes of the dual and single slat embodiments, shown in FIGS. 5, 6, and 7 were tested on male and female test subjects under simulated clinical conditions. The prototypes shown in FIGS. 5 and 6 were placed on awake male and female non-intubated healthy subjects ranging in age from 35-80 and heights of 5'2" to 6'. During this testing it was determined that in the untied state, the lack of arm flexion afforded by the upper biceps or triceps strap and cradle securing against the axilla, together with the hand guard system securing the hand in place, made objects placed on the face and torso of the subjects unreachable. With the palm secured in the hand guard system, the hand could not be disengaged and the opposing arm restraint was unable to be removed. A blood pressure cuff was able to be placed on the subjects' arms. The tested devices were adjustable, accommodating the variable arm lengths in this height category for these subjects. Non-circumferential banding at the wrist did not interfere with circulation. In the resistance band tie configuration, exercise was possible by moving the arms without being able to reach an object placed on the face or torso. In the inflexible tie configuration, exercise was possible by squeezing the palm rest. The device was described by test subjects as being comfortable.

FURTHER EMBODIMENTS AND CONSIDERATIONS

The foregoing has been a detailed description of illustrative embodiments of the invention. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present disclosure.

What is claimed is:

1. A method of using a medical protective and exercise restraint system including a rigid restraining structure, a hand strap attached to the restraining structure, and a shoulder strap attached to the restraining structure, the method comprising:
wrapping the hand strap around a patient's hand or wrist;
wrapping the shoulder strap around the patient's arm or axilla; and
positioning the restraining structure along the patient's arm such that:
the restraining structure extends from the patient's hand to above the patient's shoulder;
the restraining structure does not contact the patient; and
the patient is unable to touch their hand to their face.

2. A method of using a medical protective and exercise restraint system according to claim 1, wherein the restraint system further includes a thumb strap attached to the restraining structure and the method further comprises wrapping the thumb strap around the patient's thumb and attaching the thumb strap to the hand strap along the volar aspect of the patient's wrist or hand.

3. A method of using a medical protective and exercise restraint system according to claim 1, wherein the restraint system further includes an inflexible tie attached to the restraining structure and the method further comprises affixing the inflexible tie to a patient support structure.

4. A method of using a medical protective and exercise restraint system according to claim 3, further comprising loosening or removing the inflexible tie so that the patient can exercise and tightening or reattaching the inflexible tie to selectively increase patient restraint.

5. A method of using a medical protective and exercise restraint system according to claim 1, wherein the restraint system further includes a resistance band attached to the restraining structure and the method further comprises affixing the resistance band to a patient support structure.

6. A method of using a medical protective and exercise restraint system according to claim 4, further comprising loosening or removing the resistance band so that the patient can exercise with reduced restraint and tightening the resistance band for resistive exercising or if the patient requires increased restraint.

7. A method of using a medical protective and exercise restraint system according to claim 1, wherein the restraint system further includes a shoulder pad attached to the restraining structure or the shoulder strap and the method further comprises positioning the restraint system such that neither the restraining structure nor the shoulder pad contact the patient.

8. A method of using a medical protective and exercise restraint system according to claim 1, wherein the restraining structure includes a telescoping mechanism and the method further comprises adjusting the telescoping mechanism to change the length of the restraining structure.

9. A method of using a medical protective and exercise restraint system according to claim 1, further comprising positioning the restraining structure along the patient's arm while the patient is lying at rest on a bed with their arms alongside their body on the surface of the bed such that at least half of the restraining structure is positioned vertically above a horizontal plane passing through the patient's arm.

* * * * *